(12) United States Patent
Center et al.

(10) Patent No.: US 6,699,466 B1
(45) Date of Patent: Mar. 2, 2004

(54) IL-16 ANTAGONIST PEPTIDES AND DNA ENCODING THE PEPTIDES

(75) Inventors: David M. Center, Wellesley Hills, MA (US); William W. Cruikshank, Westford, MA (US); Hardy Kornfeld, Wellesley Hills, MA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/368,630

(22) Filed: Aug. 5, 1999

(51) Int. Cl.[7] .................. A61K 38/07; A61K 38/08; A61K 38/20; C07H 21/04
(52) U.S. Cl. .................. 424/85.2; 424/85.1; 514/2; 536/23.1; 536/23.5; 530/300
(58) Field of Search .................. 424/85.1, 85.2; 514/2, 13, 16, 17, 18; 530/300, 330, 350, 351, 325, 328, 329; 536/23.1, 23.5

(56) References Cited

U.S. PATENT DOCUMENTS

| | | | | |
|---|---|---|---|---|
| 5,350,836 A | * | 9/1994 | Kopchick et al. | .......... 530/399 |
| 5,807,712 A | * | 9/1998 | Center et al. | .............. 435/69.1 |
| 6,159,463 A | * | 12/2000 | Center et al. | .............. 424/85.2 |

FOREIGN PATENT DOCUMENTS

| | | |
|---|---|---|
| WO | WO 94/28134 | 12/1994 |
| WO | WO 99/37781 | 7/1999 |
| WO | WO 99/48514 | 9/1999 |

OTHER PUBLICATIONS

Center et al. Modualtion of lymphocyte migration by human lymphokines; identification and characterization of chemoattractan activity for lymphocytes from mitogen--stimulated mononuclear cells. J Immunol 128(6): 2563–2568, 1982.*
Cruikshank et al. Molecular and functional anaylsis of a lymphocyte chemoattractant factor: Association of biologic function with CD4 expression. Proc Natl Acad Sci USA 91: 5109–5113, 1994.*
Cruikshank et al. Lymphocyte chemoattractant factor induces CD4–dependent intracytoplasmic signaling in lymphocytes. J Immnuol. 146: 2928–2934, 1991.*
Cruikshank et al. Biological activity of interleukin–16. Nature 382(6591):501–502, 1996.*
Nicoll et al. Identification of domains in IL–16 critical for biological activity. J immunol 163: 1827–1832, 1999.*
Liu et al. Identification of a CD4 domain required for interleukin–16 binding and lymphocyte activation. J Biol Chem 274(33): 23387–23395, 1999.*
de Bie et al. Effects of interleukin–16 blocking peptide on parameters of allergic asthma in a murine model. Eur J Pharmacol 383: 189–196, 1999.*
IUIS/WJO Standing Committee on Interleukin Designation. "Interleukin 16". Eur J Immunol 26: 1196, 1995.*
Cruikshank et al. Signaling and functional properties of interleukin–16. Intern Rev Immunol 16: 523–540.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*

* cited by examiner

*Primary Examiner*—Elizabeth Kemmerer
*Assistant Examiner*—Bridget E. Bunner
(74) *Attorney, Agent, or Firm*—Scully, Scott, Murphy & Presser

(57) ABSTRACT

The present invention has found that a series of peptides having sequences that substantially correspond to specific regions of the C-terminus of IL-16 can inhibit the activity of IL-16. The present invention has demonstrated that such IL-16-inhibiting peptides can be as short as 4 amino acids in length. Based on these discoveries, the present invention provides IL-16 antagonist peptides and the use thereof for the treatment of IL-16-mediated disorders such as certain inflammatory diseases.

32 Claims, 9 Drawing Sheets

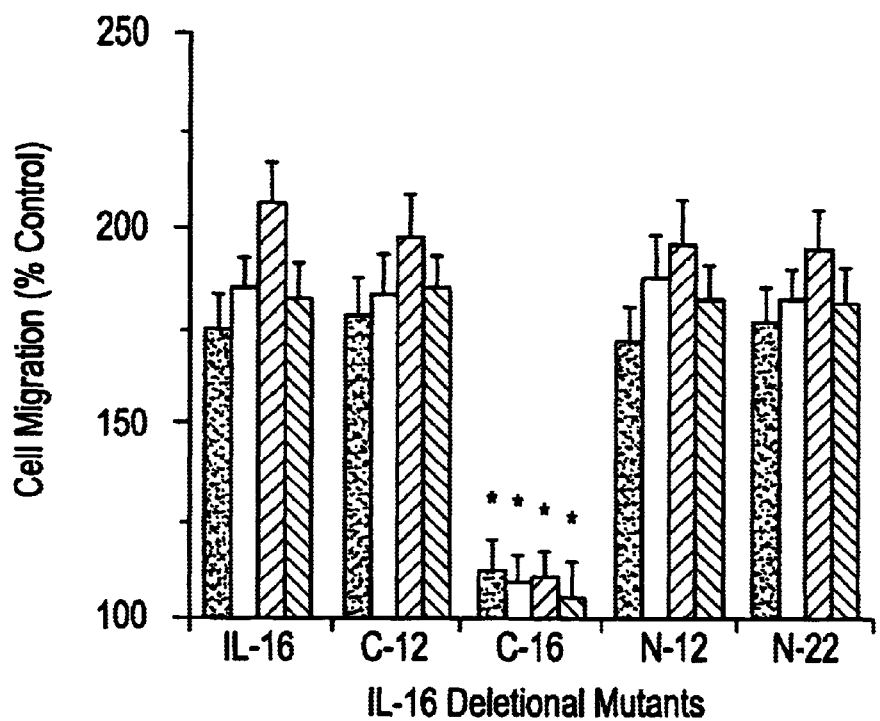
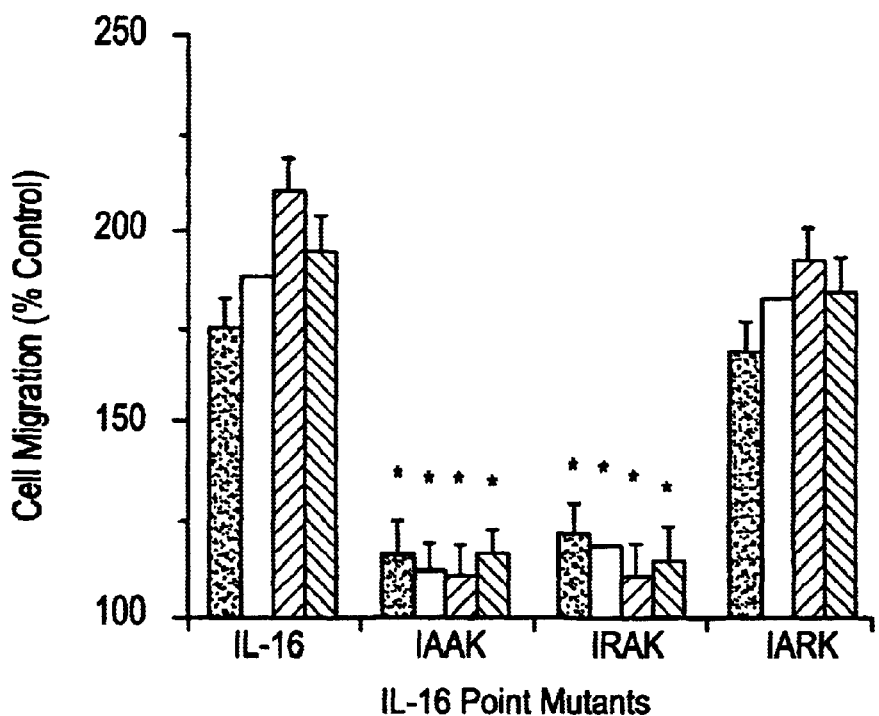

FIG. 9

Human (SEQ ID NO:39)
saasasaasd vsvestaeat vctvtlekms aglgfslegg kgslhgdkpl tinrifkgaa seqsetvqpg deilqlggta
mqgltrfeaw niikalpdgp vtivirrksl qskettaagd s Murine (SEQ ID NO:40)
saasasaasd isveskeatv ctvtlektsa glgfsleggk gslhgdkplt inrifkgdrt gemvqpgdei lqlagtavgg
ltrfeawnvi kalpdgpvti virrtslqck qttasads African green monkey = Rhesus monkey = Mangeby (SEQ ID NO:41)
saasasaasd vsvessaeat vytvtlekms aglgfslegg kgslhgdkpl tinrifkgaa seqsetiqpg deilqlagta
mqgltrfeaw niikalpdgp vtivirrksl qpkettaaad s Macaque (SEQ ID NO:42)
saasasaasd vsvessaeat vytvtlekms aglgfslegg kgslhgdkpl tinrifkgaa seqsetiqpg deilqlagta
mqgltrfeaw niikalpdgp vttvirrksl qpkettaaad s Zebu (SEQ ID NO:43)
ssgsasvdse shrireatvc tvtlektsag lgfsleggkg slhgdklltv nrilkgwleq sdtvqpgdei vhlagtamqd
ltrfeewnii kalpdgpvti vlrrkscmsk gtpaagdp Squirrel monkey (SEQ ID NO:44)
saasasaasd vsvdstaeat vctvtlekms gglgfslegg kgslqgdkpl tinrifkgaa seqsetvqpg deilhlagta
mqgltrfeaw niikalpdgp vtivikrksm qskgtsaagd Aotus trivirgatus (SEQ ID NO:45)
saasvsaasd vsvdstaeat vctvtlekms gglgfslegg kgslhgdkpl tinrifkgaa seqsetvqpg deilhlagta
mqgltrfeaw niikalpdgp vtivikrksm qskgtpaagd s

IL-16 ANTAGONIST PEPTIDES AND DNA ENCODING THE PEPTIDES

This invention was made in the course of work under grant HL32802 sponsored in part by the National Institute of Health.

FIELD OF THE INVENTION

The present invention relates to IL-16 antagonists and the use thereof for the treatment of IL-16 mediated disorders such as certain inflammatory diseases. In particular, the present invention relates to the discovery of IL-16 antagonist peptides whose sequences coincide with the C-terminal region of IL-16.

BACKGROUND OF THE INVENTION

Interleukin-16 (IL-16), previously named lymphocyte chemoattractant factor (or LCF), is a pro-inflammatory lymphokine with chemoattractant activity for resting CD4$^+$ T lymphocytes. Subsequent studies indicate that IL-16 activates signal transduction in CD4$^+$ target cells including monocytes, eosinophils and pro-B cells, and stimulates a variety of biological activities in addition to chemotaxis. Among these activities are inhibition of retroviral replication (Maciaszek, et al., *J. Immunol.* 158:5, 1997; Zhou, et al., *Nature Medicine* 3:659, 1997 and Baier, et al., *Nature* 378:563, 1995), upregulation of IL-2R and synergy with IL-2 for CD4$^+$ T cell proliferation (Parada, et al., *J. Immunol.* 160:2115, 1998), induction of RAG-1 and RAG-2 expression in CD4$^+$ pro-B cells (Szabo, et al., *J. Immunol.*, 161:2248, 1998), and transient inhibition of Mixed Lymphocyte Reaction (MLR)(Theodore, et al., *J. Immunol.* 157:1958, 1996). Investigation of certain human diseases and experimental murine models indicates that IL-16 participates in inflammatory conditions characterized by tissue recruitment of CD4$^+$T lymphocytes and other CD4$^+$ cell types. Conditions where IL-16 has been identified by ELISA and/or bioassay of body fluids, or by immunohistochemical and in situ hybridization techniques, include bronchial asthma (Laherge et al., *Am. J. Respir. Cell. Mol. Biol.* 17: 193, 1997), inflammatory bowel disease (Keates et al., *Gastroenterology* 112, A110, 1997), Graves' disease (Cruikshank et al., *J. Allergy Clin. Immunol.* 99: 554, 1997), multiple sclerosis (Biddison et al., *J. Immunol.* 158: 3046, 1997) and bullous pemphigoid (Center et al., *J. Invest. Dermatol.* 81: 204, 1983). IL-16 is also implicated in the pathogenesis of rheumatoid arthritis (Klimiuk et al., *J. Immunol.* 162: 4293–4299, 1999) and lupus (Lee et al., *British J. Rheumatology* 37: 1334–1337, 1998). Thus, it would be desirable to identify and/or generate reagents capable of interfering with the IL-16 activity for the purpose of treating inflammatory diseases.

The predicted amino acid sequence of IL-16 contains a central PDZ module, and structural studies confirm that IL-16 assumes a core PDZ-like conformation with flexible N-terminal and C-terminal tails of 17 and 14 residues, respectively (Muhlhahn et al., *Nature Structural Biology* 5:682, 1998)). A synthetic oligopeptide corresponding to the 16 C-terminal amino acids of human IL-16 (Arg106 to Ser121) has been reported to inhibit the chemoattractant activity of natural and recombinant human or murine IL-16 (Keane et al., *J. Immunol.* 160:5945, 1998).

The present invention demonstrates that a series of peptides corresponding to native or substituted sequences of the C-terminus of IL-16 can inhibit IL-16 activity. Compositions and methods useful for treating IL-16 mediated disorders are exploited using these peptides.

SUMMARY OF THE INVENTION

One embodiment of the present invention is directed to IL-16 antagonists.

Another embodiment of the present invention is directed to IL-16 antagonist peptides.

The IL-16 antagonist peptides of the present invention are at least 4 amino acids in length and substantially correspond to the C-terminal sequence of human or murine IL-16 surrounding the Arg/Lys-Arg motif, i.e., $R^{106}$–$R^{107}$ of human IL-16, $R^{103}$–$R^{104}$ of murine IL-16 or $K^{106}$–$R^{107}$ of IL-16 from squirrel monkey, for example.

A preferred IL-16 antagonist peptide of the present invention is the tetrameric peptide $X_{aa0}RX_{aa1}X_{aa2}$ (SEQ ID NO:1), wherein $X_{aa0}$ is Arg or Lys, and $X_{aa1}$ and $X_{aa2}$ can be any amino acid. Preferably, $X_{aa1}$ and $X_{aa2}$ are those amino acids found in the native sequence of a mammalian IL-16, such as Lys or Thr for $X_{aa1}$, and Ser for $X_{aa2}$.

More preferably, $X_{aa0}RX_{aa1}X_{aa2}$ is a tetramer having a sequence which coincides with the native sequence of a mammalian IL-16, e.g., RRKS (SEQ ID NO:2), RRTS (SEQ ID NO:3), or KRKS (SEQ ID NO:4). Even more preferably, such tetramer has Arg as the first amino acid. Homologs and analogs of the tetramers of SEQ ID NO:2–4 are also contemplated by the present invention. For example, analogs of RRKS (SEQ ID NO:2) include RRAS (SEQ ID NO:5) and RRKA (SEQ ID NO:6).

Another preferred IL-16 antagonist peptide of the present invention is a tetrameric peptide having the sequence of $X_{aa1}X_{aa2}X_{aa0}R$ (SEQ ID NO:8), wherein $X_{aa0}$ is Arg or Lys, and $X_{aa1}$ and $X_{aa2}$ can be any amino acid.

Preferably, $X_{aa1}$ and $X_{aa2}$ are those amino acids found in the native sequence of a mammalian IL-16, e.g., Val for $X_{aa1}$, and Ile or Leu for $X_{aa2}$.

More preferably, $X_{aa1}X_{aa2}X_{aa0}R$ is a tetramer having a sequence which coincides with the native sequence of a mammalian IL-16, such as VIRR (SEQ ID NO:9), VLRR (SEQ ID NO:10) and VIKR (SEQ ID NO:11). Even more preferably, such tetramer has Arg as the first amino acid. Homologs and analogs of these tetramers (SEQ ID NOS:9–11) are also contemplated by the present invention.

Still another preferred IL-16 antagonist peptide of the present invention is a tetrameric peptide having the sequence of $X_{aa1}X_{aa0}RX_{aa2}$ (SEQ ID NO:12), wherein $X_{aa0}$ is Arg or Lys, and $X_{aa1}$ and $X_{aa2}$ can be any one amino acid. Preferably, $X_{aa1}$ and $X_{aa2}$ are those amino acids found in the native sequence of a mammalian IL-16. For example, $X_{aa1}$ can be Ile or Leu, and $X_{aa2}$ can be Lys or Thr.

More preferably, $X_{aa1}X_{aa2}X_{aa0}R$ is a tetramer having a sequence which coincides with the native sequence of an IL-16, such as IRRK (SEQ ID NO:13), IRRT (SEQ ID NO:14), LRRK (SEQ ID NO:15), and IKRK (SEQ ID NO:16). Even more preferably, such tetramer has Arg as the first amino acid. Homologs and analogs of such tetramers are also contemplated by the present invention.

Further according to the present invention, an IL-16 antagonist peptide can be longer than a tetramer, as long as the such antagonist peptide contains one of the tetrameric sequences described hereinabove, i.e., $X_{aa0}RX_{aa1}X_{aa2}$ (SEQ ID NO:1), $X_{aa1}X_{aa0}RX_{aa2}$ (SEQ ID NO:8) or $X_{aa1}X_{aa2}X_{aa0}R$ (SEQ ID NO:12), and as long as such peptide antagonizes at least one IL-16 biological activity.

Nucleic acid molecules coding for any of the above IL-16 antagonist peptide of the present invention, expression vectors which include any of such nucleic acid molecules, as well as related host cells containing such nucleotide sequences or vectors, are also contemplated by the present invention.

In a further aspect, the present invention provides antibodies directed against the IL-16 antagonist peptides of the present invention.

Preferably, the antibodies of the present invention are raised against those IL-16 antagonist peptides whose sequences coincide with the corresponding sequences of a mammalian IL-16 protein, which antibodies can antagonize or neutralize the activity of IL-16. Both polyclonal antibodies and monoclonal antibodies are contemplated by the present invention.

Functional derivatives of the monoclonal antibodies of the present invention are also contemplated, including Fab, Fab', F(ab')$_2$ of the present mAbs, single chain antibodies, humanized antibodies and the like.

A related aspect of the present invention is directed to methods of raising antibodies specific for the IL-16 antagonist peptides of the present invention by using such peptides as immunogens.

In another embodiment, the present invention provides pharmaceutical compositions which include one or more of the IL-16 antagonist peptides or antibodies, and a pharmaceutically acceptable carrier. The pharmaceutical compositions of the present invention can also include other appropriate active ingredients, such as known anti-inflammatory agents, e.g., anti-CD4 antibodies, anti-TNFα antibodies, NSAIDS, steroids, cyclosporin-A, or cytotoxic drugs.

Another aspect of the present invention provides methods of interfering with, blocking or otherwise preventing the interaction or binding of IL-16 with an IL-16 receptor by employing the IL-16 antagonists contemplated by the present invention.

In a further aspect, the present invention provides methods of treating an IL-16-mediated disorder in a subject by administering a therapeutically effective amount of a pharmaceutical composition of the present invention. In particular, IL-16-mediated disorders which can be treated by employing the methods of the present invention include asthma, rheumatoid arthritis, inflammatory bowel disease, Graves' disease, multiple sclerosis, lupus and bullous pemphigoid.

BRIEF DESCRIPTION OF DRAWINGS

FIG. 5 depicts chemoattractant activity of mutated rIL-16. A, C-terminal and N-terminal deletion mutations. Concentrations of rIL-16 tested included $10^{-8}$ M (solid bar), $10^{-9}$ M (empty bar), $10^{-10}$ M (crosshatched bar) and $10^{-11}$ M (stippled bar). B, Chemoattractant activity of IL-16 constructs with C-terminal point mutations. The IL-16 point mutations included Arg$^{106}$ plus Arg$^{107}$ to alanine (IAAK), Arg$^{107}$ to alanine (IRAK), or Arg$^{106}$ to alanine (IARK).

FIG. 9 depicts the IL-16 sequences from various species. The IL-16 sequences from African green monkey, rhesus monkey and mangeby are identical. The Arg/Lys-Arg motif is underlined.

DETAILED DESCRIPTION OF THE INVENTION

Figure 1:
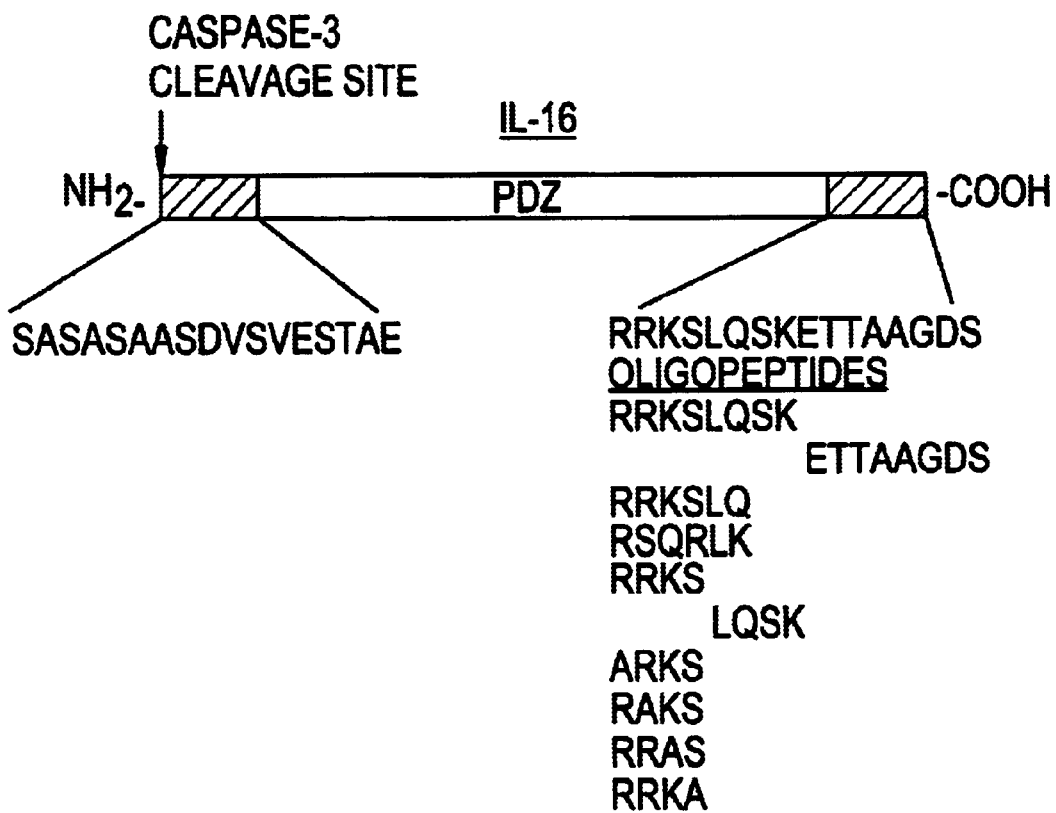
FIG. 1 graphically depicts the structure of IL-16 and peptides used for inhibition studies. Mature IL-16 (released from pro-IL-16 by caspase-3 cleavage) is a 121 amino acid polypeptide consisting of a central PDZ-like domain flanked by N-terminal and C-terminal tails (crosshatched) of 17 and 14 residues, respectively. The arginine residues at position 106 and 107 are within the boundary of the PDZ domain. The native terminal sequences are indicated below the cartoon. Oligopeptides corresponding to indicated C-terminal sequences from Arg$^{106}$ to Ser$^{121}$ were prepared. Peptides made with alanine substitutions of the native sequence are indicated in boldface.

In accordance with the present invention, it has been found that a series of peptides having sequences that substantially correspond to specific regions of the C-terminus of IL-16 can inhibit the activity of IL-16. Surprisingly, the present inventors have found that such IL-16-inhibiting peptides can be as, short as 4 amino acids in length.

Accordingly, the present invention is directed to IL-16 antagonists. By "IL-16 antagonist" is meant any molecule that inhibits, suppresses or causes the cessation of at least one IL-16-mediated biological activity by, e.g., interfering with, blocking or otherwise preventing the interaction or binding of IL-16 to an IL-16 receptor, e.g., the CD4 receptor.

"An IL-16-mediated biological activity" as used herein includes chemotaxis of CD4+cells such as CD4+T cells, inhibition of retroviral replication (such as inhibition of HIV and SIV in infected PBMCs), upregulation of IL-2R on CD4+ T cells, synergy with IL-2 for CD4$^+$ T cell proliferation, induction of RAG-1 and RAG-2 expression in CD4$^+$ pro-B cells, and inhibition of Mixed Lymphocyte Reaction (MLR). These IL-16 mediated biological activities can be determined using the assays described by Cruikshank et al. (*Proc. Natl. Acad. Sci. USA* 91: 5109–5113, 1994); Maciaszek et al. (*J. Immunol.* 158:5, 1997), Zhou, et al. (*Nature Medicine* 3:659, 1997) and Baier et al. (*Nature* 378:563, 1995); Parada et al. (*J. Immunol.* 160:2115, 1998); Szabo et al. (*J. Immunol.*, 161:2248, 1998); and Theodore et al. (*J. Immunol.* 157:1958, 1996), respectively. The teachings of these references are incorporated herein by reference.

An IL-16 antagonist functions in two ways. The antagonist can compete with IL-16 for the cell surface receptor thereby interfering with, blocking or otherwise preventing the binding of IL-16 to an IL-16 receptor. This type of antagonist, i.e., which binds the receptor but does not trigger signal transduction, is also referred to herein as a "competitive antagonist" and is a feature of the present invention. Alternatively, an IL-16 antagonist can bind to or sequester IL-16 with sufficient affinity and specificity to substantially interfere with, block or otherwise prevent binding of IL-16 to an IL-16 receptor, thereby inhibiting, suppressing or causing the cessation of at least one IL-16-mediated biological activity, such as T-cell chemotaxis, for example. This type of IL-16 antagonist, also termed a "sequestering antagonist" is more specifically described in commonly-owned, co-pending application Ser. No. 09/368,632 (pending); filed on Aug. 5, 1999 and entitled "IL-16 Antagonists", the teachings of which are incorporated herein by reference.

According to the present invention, preferred IL-16 antagonists include peptides (referred to herein as "IL-16 antagonist peptides") and antibodies.

According to the present invention, an IL-16 antagonist peptide is at least 4 amino acids in length and substantially corresponds to the C-terminal sequence of human or murine IL-16 surrounding the Arg/Lys-Arg motif, i.e., $R^{106}$–$R^{107}$ of human IL-16, $R^{103}$–$R^{104}$ of murine IL-16 or $K^{106}$–$R^{107}$ of IL16 from squirrel monkey and Aotus trivirgatus. The numbering of the amino acids are defined in accordance with the sequences of the mature, secreted form of IL-16. The sequences of the mature IL-16 from human and mouse have been described by Keane et al. (*J. Immunol* 160: 5945–5954, 1998). See also FIG. 9. The sequences of the full-length pro-IL-16 from African green monkey, rhesus monkey, mangeby, zebu, macaque, squirrel monkey and Aotus trivirgatus have been published by the Genbank database. The predicted sequences of the mature IL-16 from these species are also included in FIG. 9.

By "substantially corresponds to" is meant peptides having sequences that are identical to the native sequences of the C-terminal region of human or murine IL-16 surrounding the Arg/Lys-Arg motif, as well as homologs and analogs of such peptides.

By "homologs" is meant the corresponding peptides from IL-16 proteins of other mammalian species substantially homologous at the overall protein (i.e., mature protein) level to human or murine IL-16, so long as such homolog peptides retain the IL-16 antagonist property. The mammalian species can include African green monkey, rhesus monkey, mangeby, zebu, macaque, squirrel monkey and Aotus trivirgatus. According to the present invention, the IL-16 sequences from African green monkey, rhesus monkey and mangeby are identical and share about 95% homology with human IL-16, and about 82.1% homology with murine IL-16, respectively.

By "substantial homologous" is meant the degree of amino acid homology of at least about 65%, preferably at least about 70%, and more preferably at least about 75%, which degree is the similarity index calculated using the Lipman-Pearson Protein Alignment program with the following choice of parameters: Ktuple=2, Gap Penalty=4, and Gap Length Penalty=12.

According to the present invention, the IL-16 antagonist peptides of the present invention antagonize human and murine IL-16 as well as IL-16 molecules of other mammalian species that are substantially homologous to human or murine IL-16 proteins.

By "analogs" is meant peptides which differ by one or more amino acid alterations, which alterations, e.g., substitutions, additions or deletions of amino acid residues, do not abolish the IL-16 antagonist properties of the relevant peptides.

Thus, an analog of a peptide can have one or more amino acid residues of the peptide substituted, conservatively or non-conservatively. Examples of conservative substitutions include the substitution of a non-polar (hydrophobic) residue such as I, V, L or M for another; the substitution of one polar (hydrophilic) residue for another polar residue, such as R for K, Q for N, G for S, or vice versa; and the substitution of a basic residue such as K, R or H for another or the substitution of one acidic residue such as D or E for another. Examples of non-conservative substitutions include the substitution of a non-polar (hydrophobic) residue such as I, V, L, A, M for a polar (hydrophilic) residue such as C, Q, D, K and/or vice versa.

The phrase "analog" also includes the use of chemically derivatized residues in place of a non-derivatized residue as long as the peptide retains the requisite IL-16 antagonist properties.

Analogs also include addition of amino acids to the N-terminus or C-terminus of a relevant peptide. For example, the addition of cysteine to the N- or C-terminus of a peptide, by which, if desired, the peptide can be covalently attached to a carrier protein, e.g., albumin. Such attachment, it is believed, can minimize clearing of the peptide from the blood and also prevent proteolysis of the peptides.

In addition, for purposes of the present invention, peptides containing D-amino acids in place of L-amino acids are also included in the term "analogs". The presence of such D-isomers may help minimize proteolytic activity and clearing of the peptide.

A preferred IL-16 antagonist peptide of the present invention is a tetrameric peptide having the sequence of $X_{aa0}RX_{aa1}X_{aa2}$ (SEQ ID NO:1), wherein $X_{aa0}$ is Arg or Lys, and $X_{aa1}$ and $X_{aa2}$ can be any amino acid, which includes A=Ala=Alanine, R=Arg=Arginine,
N=Asn=Asparagine,
D=Asp=Aspartic acid,
C=Cys=Cysteine,
Q=Gln=Glutamine,
E=Glu=Glutamic acid,
G=Gly=Glycine,
H=His=Histidine,
I=Ile=Isoleucine,
L=Leu=Leucine,
K=Lys=Lysine,
M=Met=Methionine,
F=Phe=Phenylalanine,
P=Pro=Proline,
S=Ser=Serine,
T=Thr=Threonine,
W=Trp=Tryptophan,
Y=Tyr=Tyrosine and
V=Val=Valine.

Preferably, $X_{aa1}$ and $X_{aa2}$ are those amino acids found in the native sequence of a mammalian IL-16. For example, $X_{aa1}$ can be Lys (human, African green monkey, rhesus monkey, mangeby, zebu, macaque, squirrel monkey and Aotus trivirgatus) or Thr (murine), and $X_{aa2}$ can be Ser (human, African green monkey, rhesus monkey, mangeby, zebu, macaque, squirrel monkey, Aotus trivirgatus and murine).

More preferably, $X_{aa0}RX_{aa1}X_{aa2}$ is a tetramer having a sequence which coincides with the native sequence of a mammalian IL-16. Examples of such tetrameric sequences include RRKS (SEQ ID NO:2) (human, African green monkey, rhesus monkey, mangeby, zebu and macaque), RRTS (SEQ ID NO:3) (murine), and KRKS (SEQ ID NO:4) (squirrel monkey and Aotus trivirgatus).

Even more preferably, $X_{aa0}RX_{aa1}X_{aa2}$ coincides with the native sequence of a mammalian IL-16 and $X_{aa0}$ is Arg, for example, RRKS (SEQ ID NO:2) and RRTS (SEQ ID NO:3).

Homologs and analogs of any of these tetramers SEQ ID NOS:2–4 are also contemplated by the present invention. For example, analogs of tetramer RRKS (SEQ ID NO:2) of the present invention include RRAS (SEQ ID NO:5) and RRKA (SEQ ID NO:6), and an analog of RRTS (SEQ ID NO:3) is RRAS (SEQ ID NO:5) and RRTA (SEQ ID NO:7).

Another preferred IL-16 antagonist peptide of the present invention is a tetrameric peptide having the sequence of $X_{aa1}X_{aa2}X_{aa0}R$ (SEQ ID NO: 12), wherein $X_{aa0}$ is Arg or Lys, and $X_{aa1}$ and $X_{aa2}$ can be any amino acid.

Preferably, $X_{aa1}$ and $X_{aa2}$ are those amino acids found in the native sequence of a mammalian IL-16. For example, $X_{aa1}$ can be Val (human, African green monkey, rhesus monkey, mangeby, zebu, macaque, squirrel monkey, Aotus trivirgatus and murine), and $X_{aa2}$ can be Ile (human, African green monkey, rhesus monkey, mangeby, macaque, squirrel monkey, Aotus trivirgatus and murine), or Leu (zebu).

More preferably, $X_{aa1}X_{aa2}X_{aa0}R$ (SEQ ID NO:8) coincides with the native sequence of a mammalian IL-16. Examples of such tetrameric sequences include VIRR (SEQ ID NO:9) (human, African green monkey, rhesus monkey, mangeby, macaque and murine), VLRR (SEQ ID NO:10) (Zebu), and VIKR (SEQ ID NO:11) (squirrel monkey and Aotus trivirgatus).

Even more preferably, $X_{aa1}X_{aa2}X_{aa0}R$ coincides with the native sequence of a mammalian IL-16 and $X_{aa0}$ is Arg, for example, VIRR (SEQ ID NO:9) and VLRR (SEQ ID NO:10).

Homologs and analogs of these tetramers (SEQ ID NOS: 9–11) are also contemplated by the present invention.

Still another preferred IL-16 antagonist peptide of the present invention is a tetrameric peptide having the sequence of $X_{aa1}X_{aa0}RX_{aa2}$ (SEQ ID NO: 12), wherein $X_{aa0}$ is Arg or Lys, and $X_{aa1}$ and $X_{aa2}$ can be any amino acid.

Preferably, $X_{aa1}$ and $X_{aa2}$ are those amino acids found in the native sequence of a mammalian IL-16. For example, $X_{aa1}$ can be Ile (human, African green monkey, rhesus monkey, mangeby, macaque, squirrel monkey, Aotus trivirgatus and murine) or Leu (zebu), and $X_{aa2}$ can be Lys (human, African green monkey, rhesus monkey, mangeby, macaque, zebu, squirrel monkey and Aotus trivirgatus) or Thr (murine).

More preferably, $X_{aa1}X_{aa2}X_{aa0}R$ (SEQ ID NO:12) coincides with the native sequence of an IL-16. Examples of such tetrameric sequences include IRRK (SEQ ID NO:13) (human, African green monkey, rhesus monkey, mangeby and macaque), LRRK (SEQ ID NO:15) (zebu), IKRK (SEQ ID NO:16) (squirrel monkey and Aotus trivirgatus), and IRRT (SEQ ID NO:14) (murine).

Even more preferably, $X_{aa1}X_{aa0}RX_{aa2}$ (SEQ ID NO:12) coincides with the native sequence of a mammalian IL-16 and $X_{aa0}$ is Arg, for example, IRRK (SEQ ID NO:13), LRRK (SEQ ID NO:15) and IRRT (SEQ ID NO:14).

Homologs and analogs of such tetramers (SEQ ID NOS:13–16) are also contemplated by the present invention.

Further according to the present invention, an IL-16 antagonist peptide can be longer than a tetramer, as long as such antagonist peptide contains one of the tetrameric sequences described hereinabove, i.e., $X_{aa0}RX_{aa1}X_{aa2}$ (SEQ ID NO:1), $X_{aa1}X_{aa0}RX_{aa2}$ (SEQ ID NO:12) or $X_{aa1}X_{aa2}X_{aa0}R$ (SEQ ID NO: 8), and as long as such peptide antagonizes at least one IL-16 biological activity. Preferably, the peptides contain $X_{aa0}RX_{aa1}X_{aa2}$ (SEQ ID NO:1), more preferably, $X_{aao}$ is Arg in SEQ ID NO:1. Generally speaking, the peptide has less than 35 amino acids, preferably less than 25 amino acids, more preferably less than 16 amino acids. The, peptides of the present invention does not include RRKSLQSKETTAAGDS (SEQ ID NO:33).

Preferred antagonist peptides include those having sequences which coincide with the native C-terminal sequence of an IL-16 starting from the residue Arg/Lys, which is Arg[106] for human IL-16, or the corresponding positions of other mammalian IL-16 molecules. Examples of such peptides include 6-mers RRKSLQ (SEQ ID NO:17), RRTSLQ (SEQ ID NO:18), RRKSCM (SEQ ID NO:19), KRKSMQ (SEQ ID NO:20), 8-mers RRKSLQSK (SEQ ID NO:24), RRTSLQCK (SEQ ID NO:25), RRKSLQPK (SEQ ID NO:26), RRKSCMSK (SEQ ID NO:27), and KRKSM-QSK (SEQ ID NO:28). Preferred peptides include RRKSLQ (SEQ ID NO:17), RRTSLQ (SEQ ID NO:18), RRKSCM (SEQ ID NO:19), RRKSLQSK (SEQ ID NO:24), RRTSLQCK (SEQ ID NO:25), RRKSLQPK (SEQ ID NO:26), and RRKSCMSK (SEQ ID NO:27). Homologs and analogs of any of these tetramers are also contemplated by the present invention.

The IL-16 antagonist peptides of the present invention can be made by a variety of well known techniques. For example, the peptides can be chemically synthesized using standard solid-phase synthetic techniques, initially described by Merrifield in *J. Am. Chem. Soc.* 85:2149–2154 (1963), or the solution methods as described in *The Proteins*, Vol. II. 3d Ed., Neurath, H. et al., Eds., p. 105–237, Academic Press, New York, N.Y. (1976). See also Bodanszky, et al. *Peptide Synthesis*, John Wiley & Sons, 2d Ed., (1976); and J. Stuart and J. D. Young, *Solid Phase Peptide Synthesis*, Pierce Chemical Company, Rockford, Ill., (1984). Appropriate protective groups for use in different peptide syntheses are described in the above-mentioned texts as well as in J. F. W. McOmie, Protective Groups in *Organic Chemistry*, Plenum Press, New York, N.Y. (1973).

Additionally, the peptides of the present invention can also be prepared by recombinant DNA techniques. Nucleotide sequences coding for peptides of the present invention can be readily made by those skilled in the art and then inserted into an expression vector for producing the subject peptide in an appropriate host cell. Recombinantly produced peptides can be purified following routine procedures.

Nucleic acid molecules coding for an IL-16 antagonist peptide of the present invention, and expression vectors which include any of such nucleic acid molecules, as well as related host cells containing such nucleotide sequences or vectors, are also contemplated by the present invention.

In a further aspect, the invention provides antibodies raised against the IL-16 antagonist peptides of the present invention. The antibodies of the present invention do not include mAb14.1 or mAb 17.1 (see, Cruikshank et al., *Proc. Natl. Acad. Sci. USA* 91(11):5109–5113, 1994 Hessel et al., *J. Immunol.* 160: 2998–3005, 1998 and Keane et al., *J. Immunol.* 160: 5945–5954, 1998).

Preferably, the antibodies of the present invention are raised against those IL-16 antagonist peptides whose sequences coincide with the corresponding sequences of a mammalian IL-16 protein, preferably, human IL-16. According to the present invention, such antibodies can also inhibit the IL-16 function by binding to the peptide epitopes of an IL-16 molecule required for interacting with an IL-16 receptor, thereby blocking and neutralizing at least one IL-16-mediated biological activity. The antibodies of the present invention do not include mAb14.1 or mAb 17.1 (see, Hessel et al., *J. Immunol.* 160: 2998–3005, 1998, and Keane et al., *J. Immunol.* 160: 5945–5954, 1998).

The antibodies of the present invention can be generated by well-known methods. The peptides, in combination with Freund's adjuvant, can be injected into an appropriate animal such as rabbit, mice, cow, guinea pig, rat, donkey and the like. The peptides can be coupled to a carrier polypeptide, e.g., KLH, prior to immunization as described in Ausubel et al. (1989) *Current Protocols in Molecular Biology*, John Wiley & Sons, New York.

Both polyclonal antibodies and monoclonal antibodies can be prepared using the immunized animal. The procedure for making polyclonal and monoclonal antibodies is well known in the art and can be found in, e.g., Harlow, E. and Lane, D., *Antibodies: A Laboratory Manual*, Cold Spring Harbor Press, 1988. Polyclonal antibodies can be readily purified from the serum of the immunized animal using a number of well known protein purification procedures such as affinity chromatography. Monoclonal clonal antibodies can be prepared by following the standard hybridoma techniques (see e.g. Kohler et al., *Nature* 256:495, 1975). Briefly, the spleens of the immunized animal can be removed, and their lymphocytes fused to an immortal cell line. The resulting hybridomas can be screened initially by binding affinity to the relevant peptide antigen, which can be determined by various immuno assays such as ELISA. Hybridomas that produce monoclonal antibodies specific for the relevant peptide antigen can be further screened for the ability of inhibiting at least one IL-16 mediated biological activity, such as chemotaxis of CD4+ T cells. Such IL-16-inhibiting antibodies are considered to be useful antagonists in the invention.

Functional derivatives of the monoclonal antibodies of the present invention are also contemplated. "Functional derivatives" refer to antibody molecules or fragments thereof that are derived from the instant monoclonal antibodies and that have retained the antigen specificity of the instant monoclonal antibodies. Examples of functional derivatives include Fab, Fab', F(ab')$_2$ of the present mAbs, single chain antibodies, humanized antibodies and the like.

A single-chain antibody (SAb) is created by fusing together the variable domains of the heavy and light chains using a short peptide linker, thereby reconstituting an antigen binding site on a single molecule. Such single-chain antibody variable fragments (Fvs) can be fused to all or a portion of the constant domains of the heavy chain of an immunoglobulin molecule, if necessary. The use of sAb avoids the technical difficulties in the introduction of more than one gene construct into host cells. Single chain antibodies and methods for their production are known in the art. See, e.g., Bedzyk et al. (1990) *J. Biol. Chem.*, 265:18615; Chaudhary et al. (1990) *Proc. Natl. Acad. Sci.*, 87:9491; U.S. Pat. No. 4,946,778 to Ladner et al.; and U.S. Pat. No. 5,359,046 to Capon et al.

The monoclonal antibodies of the present invention can be humanized to reduce the immunogenicity for use in humans. For example, to humanize a monoclonal antibody raised in mice, one approach is to make mouse-human chimeric antibodies having the original variable region of the murine mAb, joined to constant regions of a human immunoglobulin. Chimeric antibodies and methods for their production are known in the art. See, e.g., Cabilly et al., European Patent Application 125023 (published Nov. 14, 1984); Taniguchi et al., European patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Robinson et al., International Patent Publication #PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988). These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes. Humanized antibodies can be made using a second approach, i.e., to construct a reshaped human antibody, which has been described in, e.g., Maeda et al., *Hum. Antibod. Hybridomas* 2: 124–134, 1991, and Padlan, *Mol. Immunol.* 28: 489–498, 1991.

A related aspect of the present invention is directed to methods of generating antibodies specific for the IL-16 antagonist peptides of the present invention by using such peptides as immunogens.

In another embodiment of the present invention, one or more IL-16 antagonists, e.g., IL-16 antagonist peptides or antibodies, are included in pharmaceutical compositions. Such pharmaceutical compositions are used in the treatment of IL-16 mediated disorders, such as IL-16 mediated inflammatory diseases.

The pharmaceutical compositions of the present invention can also include other appropriate active ingredients, such as known anti-inflammatory agents, e.g., anti-CD4 antibodies, anti-TNFα antibodies, NSAIDS, steroids, cyclosporin-A or cytotoxic drugs.

According to the present invention, the pharmaceutical compositions also includes a pharmaceutically acceptable carrier.

As used herein, a pharmaceutically acceptable carrier includes any and all solvents, dispersion media, isotonic agents and the like. Except insofar as any conventional media, agent, diluent or carrier is detrimental to the recipient or to the therapeutic effectiveness of the active ingredients contained therein, its use in practicing the methods of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

In accordance with the present invention, the active ingredients of the present pharmaceutical compositions can be combined with the carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like. When appropriate, the pharmaceutical compositions of the present invention should be made sterile by well known procedures. For example, solutions can be made sterile by filter sterilization or autoclave. To obtain a sterile powder, sterilized solutions can be vacuum-dried or freeze-dried as necessary.

Another embodiment of the present invention provides methods of interfering with, blocking or otherwise preventing the interaction or binding of IL-16 with an IL-16 receptor by employing the IL-16 antagonists contemplated by the present invention.

In a further aspect of the present invention, the pharmaceutical compositions of the present invention are employed for the treatment of IL-16 mediated pathological disorders. Thus, the present invention provides methods of treating an IL-16-mediated disorder in a subject by administering a therapeutically effective amount of a pharmaceutical composition of the present invention.

By "an IL-16-mediated disorder" is meant a pathological disorder, the onset, progression or the persistence of the symptoms of which requires the participation of IL-16 molecules. Particularly, IL-16-mediated disorders contemplated by the present invention include asthma, rheumatoid arthritis, inflammatory bowel disease, Graves' disease, multiple sclerosis, lupus and bullous pemphigoid.

The term "treatment" refers to effective inhibition of the IL-16 activity so as to prevent or delay the onset, retard the progression or ameliorate the symptoms of the disorder.

The term "subject" refers to any mammalian subject. Preferably, the subject is a human subject.

According to the present invention, for treating an IL-16-mediated disorder in a mammalian subject, preferred pharmaceutical compositions for use are those constituted with IL-16 antagonist peptides or antibodies that effectively antagonize the function of the IL-16 molecule of such mammalian species.

The term "therapeutically effective amount" means the dose required to effect an inhibition of the IL-16 activity so as to prevent or delay the onset, slow down the progression or ameliorate the symptoms of the disorder.

Precise dosages depend on depends on the disease state or condition being treated and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of a pharmaceutical composition for the administration to adult humans ranges from about 0.001 mg to about 20 mg per kilogram of body weight, more preferably, in the range of about 0.01 mg to about 5 mg per kilogram of body weight. The peptides should preferably be administered in an amount of at least about 50 mg per dose, more preferably in an amount up to about 500 mg per dose. Since the peptide compositions of this invention will eventually be cleared from the bloodstream, re-administration of the compositions may be required. Alternatively, implantation or injection of the peptides provided in a controlled release matrix can be employed.

The pharmaceutical compositions of the present invention can be administered to the subject in any practical and convenient manner. The routes of administration which can be employed include the oral, ophthalmic nasal, topical, transdermal, or parenteral (e.g., intravenous, intraperitoneal, intradermal, subcutaneous or intramuscular). In addition, the pharmaceutical compositions can be introduced into the body, by injection or by surgical implantation or attachment, proximate to a preselected tissue or organ site such that a significant amount of an active substance is able to enter the site by direct diffusion, and preferably, in a controlled release fashion.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are possible within the scope of the invention. All the publications mentioned in the present disclosure are incorporated herein by reference.

EXAMPLE 1

Materials and Methods

Peptides

Synthetic oligopeptides corresponding to native or altered C-terminal IL-16 sequences were made at the commercial facilities of Research Genetics, Inc. (Atlanta, Ga.).

Cell Preparation

Human peripheral blood mononuclear cells (PBMC) were isolated as described (Center, et al., *J. Immunol.* 128:256, 1982; Cruikshank, et al., *J. Immunol.* 128:2569, 1982 and Cruikshank, et al., *J. Immunol.* 138:3817, 1987) from the blood of healthy volunteers by density centrifugation on Ficoll-Paque reagent (Pharmacia, Piscataway, N.J.). The mononuclear cell layer was washed with medium 199 (M.A. Bioproducts, Walkersville, Md.) supplemented with 0.4% bovine serum albumin, 25 mM HEPES buffer, and 100 U/ml of penicillin and 100 $\mu$g/ml streptomycin (M199-HPS). Samples were enriched for T lymphocytes by nylon wool adherence as described (Julius, et al., *Eur. J Immunol* 3:645, 1973). The nonadherent cells were >95% $CD3^+$ as determined by flow cytometry.

Recombinant Proteins

Recombinant human IL-16 corresponding to the 121 C-terminal amino biologically active cytokine cleaved from natural pro-IL-16 was produced in *E. coli* as a polyhistidine fusion protein using the expression vector pET-30 LIC (Novagen, Madison, Wis.). Following lysis of transformed bacteria, the protein was purified by metal chelation chromatography and the N-terminal polyhistidine tag was removed by cleavage with enterokinase.

The native IL-16 expression vector (pET-30/IL-16$^{121}$) was used as a template for PCR mutagenesis to create four recombinant IL-16 (rIL-16) mutant constructs with progressive four amino acid deletions at the C-terminus (C-4 to C-16), as well as deletions of 12 or 22 N-terminal residues. Two double deletion constructs lacking the first 12 or 22 N-terminal residues as well as the last 16 C-terminal residues of IL-16 were also produced. Point mutations in C-terminal residues of rIL-16 were generated by site-directed mutagenesis using the Stratagene Quick Change Kit (Stratagene, La Jolla, Calif.) according to the manufacturer's specifications. The point mutations included alanine substitution for Arg$^{106}$, Arg$^{107}$, and Arg$^{106}$ plus Arg$^{107}$.

Western Blot Analysis

Native and mutated rIL-16 proteins were subjected to electrophoresis through a 15% SDS-polyacrylamide gel, then electrophoretically transferred to nitrocellulose membranes. The membranes were probed with either polyclonal rabbit anti-rIL-16 or a murine anti-rIL-16 mAb designated clone 17.1. Secondary horse radish peroxidase (HRP)-conjugated anti-immunoglobulins were used at a concentration of 1:5000, and the signal was visualized by chemiluminescence (Pierce, Rockford, Ill.).

Chemotaxis Assay

Cell migration was measured using a modified Boyden chemotaxis chamber as described (Center, et al., *J. Immunol.* 128:256, 1982; Cruikshank, et al., *J. Immunol.* 128:2569, 1982, and Cruikshank, et al., *J. Immunol.* 138:3817, 1987). Cells were suspended ($5 \times 10^6$ cells/ml) in M199-HPS and loaded into the upper wells, separated by an 8 $\mu$m pore size nitrocellulose membrane from lower wells. The lower wells were loaded with control buffer or experimental chemoattractant stimuli, with or without synthetic peptides. After a 4 h incubation at 37° C., the membranes were removed and stained with hematoxylin, dehydrated by sequential washes in ethanol and propanol, then washed in xylene to clarify the filter for cell counting by light microscopy. Cell migration was quantified by counting the number of cells in the filter that had moved beyond a depth of 50 $\mu$m in five separate fields in duplicate wells for all conditions. Cell counts were compared with unstimulated control cell migration which was normalized to 100%. Results are expressed as mean % control migration and the data analyzed for statistical significance ($P<0.05$) by Student's t test.

Mixed Lymphocyte Reaction

Stimulator cells for mixed lymphocyte reactions were prepared by incubating PBMC ($10^6$/ml) with 25 $\mu$g/ml mitomycin C for 30 min. The cells were then washed four times with RPMI 1640 medium supplemented with 25 mM HEPES buffer, 100 U/ml penicillin, and 100 $\mu$g/ml streptomycin (RPMI 1640-HPS), then resuspended in RPMI 1640-HPS supplemented with 10% fetal bovine serum (complete medium) at $10^6$ cells/ml. Responder cells were prepared from an unrelated donor, suspended in complete medium at $10^6$ cells/ml, and pre-incubated (1 h, 37° C.) with control buffer, or with rIL-16 or mutated rIL-16 constructs ($10^{-9}$ M to $10^{-11}$ M). Stimulator cells were then added (1:1) and the cell mixtures were transferred in quadruplicate to 96-well round-bottom plates. Cell cultures were pulsed with [$^3$H] thymidine on day 5, harvested with a Titertek cell harvester, and counted in a Becton Dickinson scintillation counter on day 6. Results are expressed as mean % cpm above background ± SEM. Data were analyzed for statistical significance ($P<0.05$) by Student's t test.

EXAMPLE 2

Inhibition of IL-16-Stimulated T Lymphocyte Motility by C-terminal Oligopeptides A series of oligopeptides derived from the 16 C-terminal of human IL-16 residues were prepared (FIG. 1) and tested for their ability to stimulate the T lymphocyte motility using a modified Boyden chemotaxis chamber assay.

Figure 2A:
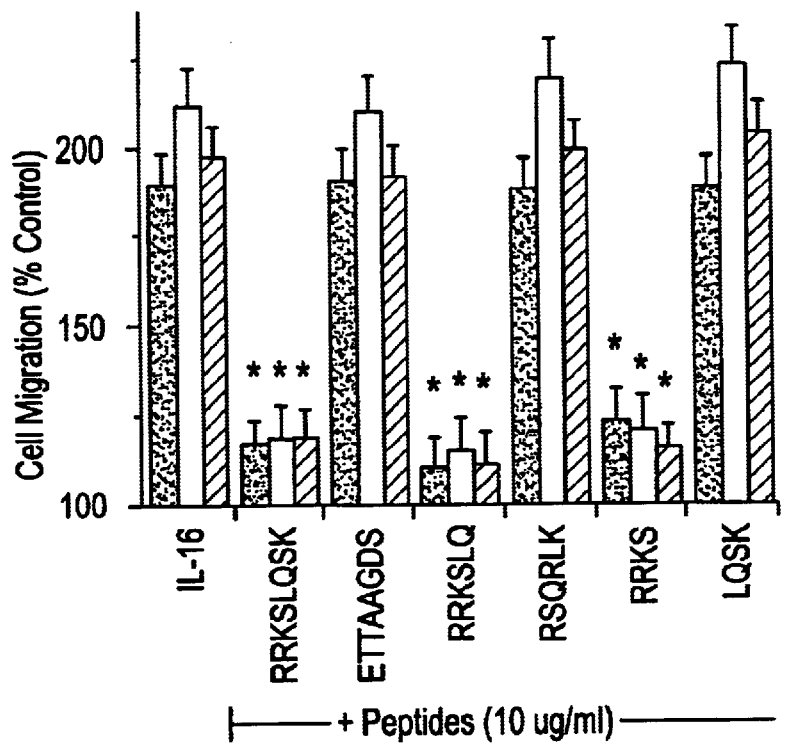
FIG. 2 depicts the inhibition of IL-16-stimulated T cell motility by C-terminal peptides in chemotaxis assays using human T lymphocytes in the presence or absence of C-terminal peptides. A, IL-16 inhibition by oligopeptides corresponding to native IL-16 sequences. Cell migration in response to rIL-16 at concentrations of $10^{-9}$ M (solid bar), $10^{-10}$ M (empty bar) and $10^{-11}$ M (crosshatched bar) with or without peptides was compared to cell migration in response to control buffer (considered as 100%). Each of the indicated peptides was added at 10 μg/ml. Ten high-power fields were counted and the mean obtained for each condition. Results are expressed as the mean % control migration ± SEM for three experiments. Comparisons between control and experimental conditions were analyzed by Student's t test; the asterisk indicates statistical significance (P<0.05) for a difference in T cell migration at the indicated IL-16 concentration in the presence or absence of peptide. B, IL-16 inhibition by oligopeptides with alanine substitutions. Results are expressed as the mean % control migration ± SEM for four experiments.
Figure 2B:
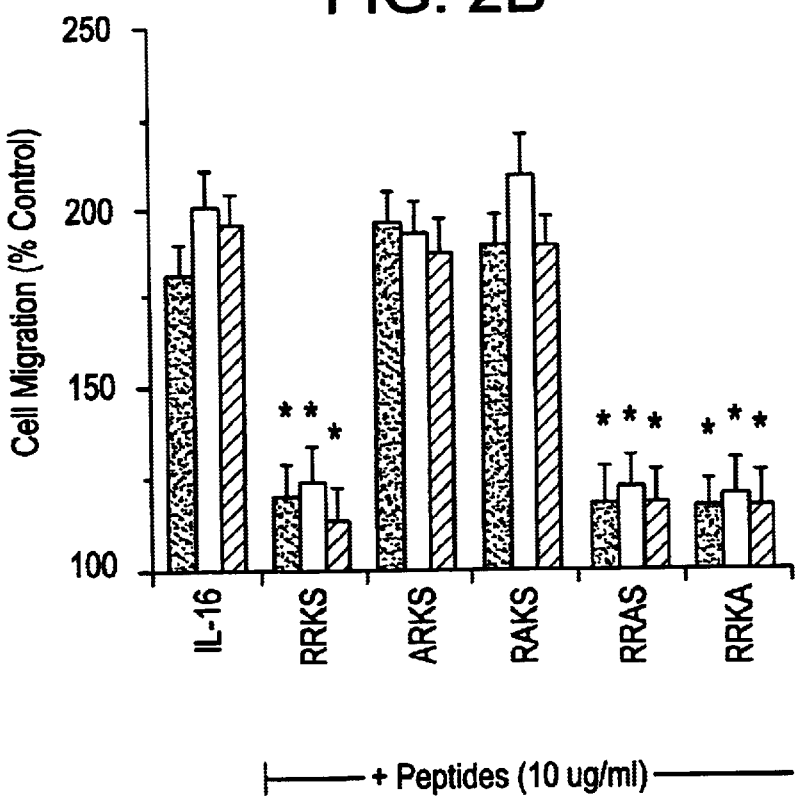

Human T lymphocytes were loaded in the upper wells, and rIL-16 at concentrations of $10^{31\ 9}$ M, $10^{-10}$ M or $10^{-11}$ M was loaded in the lower wells, in the presence or absence of two 8-mer peptides corresponding to amino acids Arg$^{106}$ to Lys$^{113}$ (SEQ ID NO:24), and Glu$^{114}$ to Ser$^{121}$ (SEQ ID NO:46) of IL-16. As shown in FIG. 2,A, only the Arg$^{106}$ to Lys$^{113}$ peptide (SEQ ID NO:24) inhibited IL-16 in this assay. The six-mer RRKSLQ (SEQ ID NO:17) also inhibited IL-16-stimulated T cell migration, but a scrambled peptide containing the same residues in a randomly chosen sequence (SEQ ID NO:47) demonstrated no inhibitory activity. To further define the residues mediating inhibition, the eight residue sequence from Arg$^{106}$ to Lys$^{113}$ was divided into RRKS (SEQ ID NO:2) and LQSK (SEQ ID NO:48). Only RRKS (SEQ ID NO:2) inhibited IL-16 chemoattractant activity (FIG. 2,A).

The contribution of individual residues within RRKS was analyzed by alanine scanning (FIG. 2,B). Substitution of either Arg$^{106}$ or Arg$^{107}$ was associated with loss of inhibitory activity against IL-16-induced chemotaxis. In contrast, the peptides RRAS (SEQ ID NO:5) and RRKA (SEQ ID NO:6) inhibited IL-16 as effectively as the native RRKS (SEQ ID NO:2).

Figure 3:
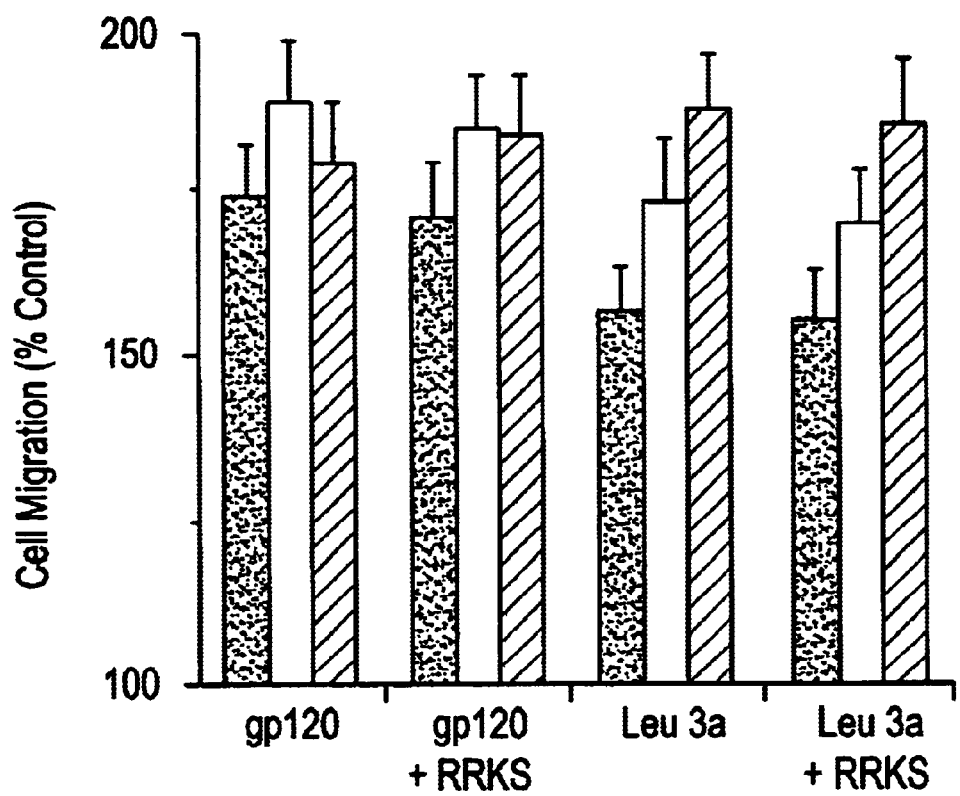
FIG. 3 depicts specific inhibition of IL-16 by peptides. T cells were stimulated with gp120 or Leu 3a at 0.5 μg/ml (solid bars), 1.0 μg/ml (empty bars) and 5.0 μg/ml (crosshatched bars) in the presence or absence of peptide RRKS (10 μg/ml) as indicated. Results are expressed as the mean % control migration ± SEM for three experiments.

To test whether inhibition by RRKS (SEQ ID NO:2) of chemotaxis in response to CD4 stimulation is specific for IL-16, peptide RRKS (SEQ ID NO:2) was tested in combination with two different CD4 ligands that induce T cell motility, HIV-1 gp120 (strain HIV-1$_{3B}$) and Leu 3a mAb. Cell migration in response to HIV-1 gp120 (13), or divalent anti-CD4 mAb Leu 3a was not blocked by this peptide (FIG. 3).

These data demonstrate that the four-residue peptide RRKS can effectively and specifically inhibit the chemoattractant activity of IL-16.

EXAMPLE 3

Chemoattractant Activity of IL-16 Deletion Mutants

Figure 4:
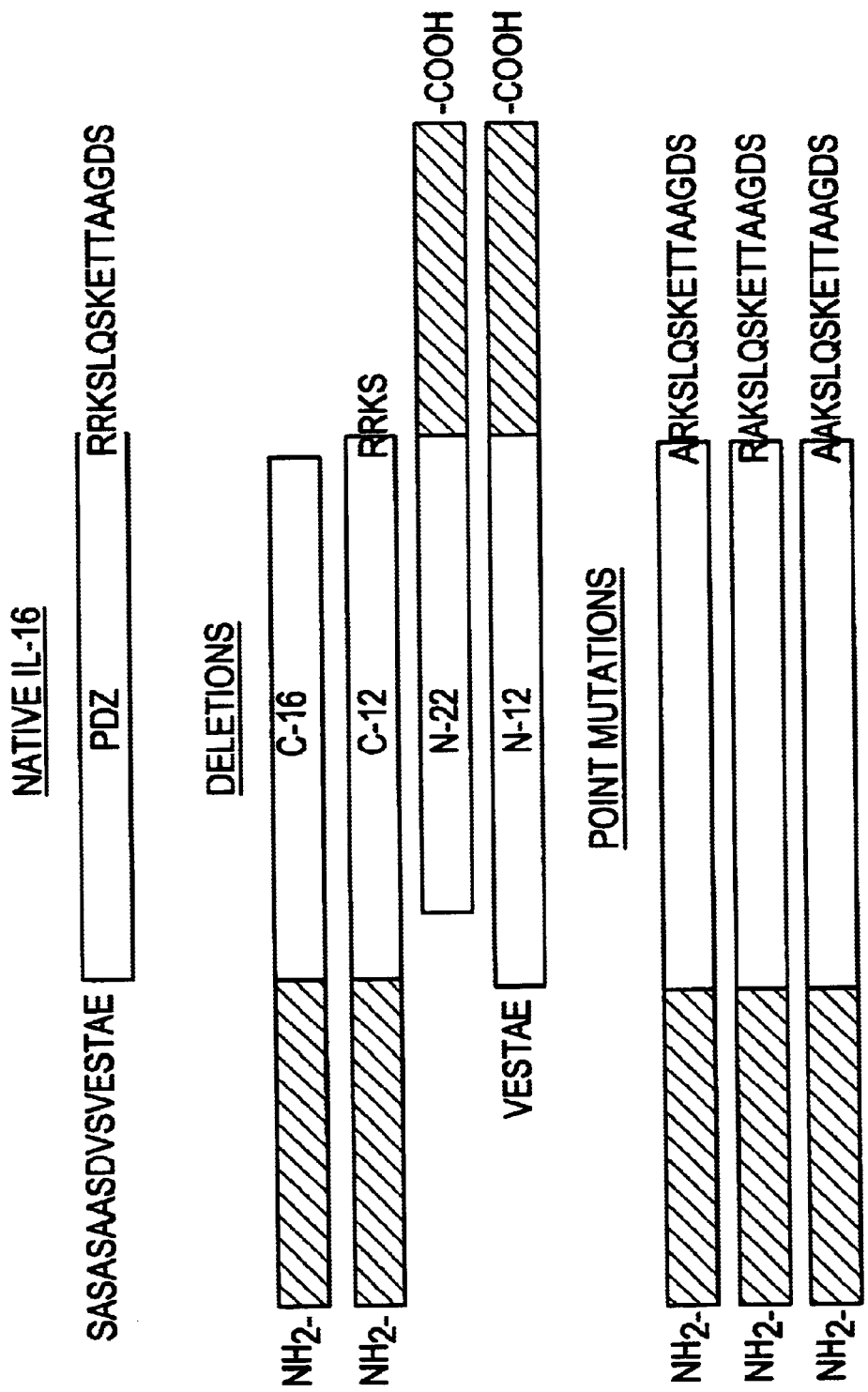
FIG. 4 graphically depicts composition of recombinant IL-16 mutants generated by PCR mutatgenesis and produced in E. coli. The native N-terminal and C-terminal sequences are represented as crosshatched bars flanking the central PDZ-like core. Deletions of 12 or 16 C-terminal residues and 12 or 22 N-terminal residues are shown in the figure. Mutants with single Alanine substitutions are also indicated.

IL-16 mutant constructs were created with progressive deletions of 4 C-terminal amino acids from C-4 through C-16 (FIG. 4). The C-12 construct terminates at Ser$^{108}$, retaining the RRKS motif. The C-16 construct terminates at Ile$^{105}$, deleting RRKS and succeeding downstream residues. These mutant IL-16 molecules were tested in chemotaxis assays. As shown in FIG. 5, A, C-12 was active as native rIL-16, while the C-16 deletion completely eliminated the chemoattractant activity. In similar experiments, C-4 and C-8 deletion constructs demonstrated chemoattractant activities comparable to native rIL-16. These results, consistent with the peptide studies, indicate that residues within the RRKS motif are required for IL-16-stimulated chemoattractant activity.

To determine whether the N-terminal structures of Il-16 contribute to chemotactic signaling, two additional constructs with deletion of 12 or 22 N-terminal amino acids were tested. Both the N-12 and N-22 deletion mutants demonstrated chemoattractant activity comparable to native IL-16 (FIG. 5,A). These results indicate that the N-terminal domain is not required in receptor interactions activating cell motility.

EXAMPLE 4

Contribution of Specific C-terminal Residues to IL-16 Chemoattractant Activity

To determine the contribution of individual residues within the RRKS motif to chemoattractant signaling, and to test the activity of IL-16 mutants with minimal structural alterations, a series of point mutations using alanine substitution were generated (FIG. 4). Replacement of Arg$^{107}$ alone, or Arg$^{106}$ plus Arg$^{107}$, completely abrogated chemoattractant activity of the recombinant protein (FIG. 5,B). In contrast, substitution of Arg$^{106}$ alone retained full activity. The identical pattern of motile responses was observed using a different IL-16-responsive cell type, human peripheral blood monocytes.

To test whether multimer formation is disrupted by deletion or point mutation, the above-generated mutant IL-16 molecules were assessed by HPLC. All of these constructs formed multimers similar to native IL-16. These observations indicate that mutation of Arg$^{107}$ directly interferes with CD4 binding or activation by IL-16.

EXAMPLE 5

Western Analysis of IL-16 Mutant Proteins

Figure 6:
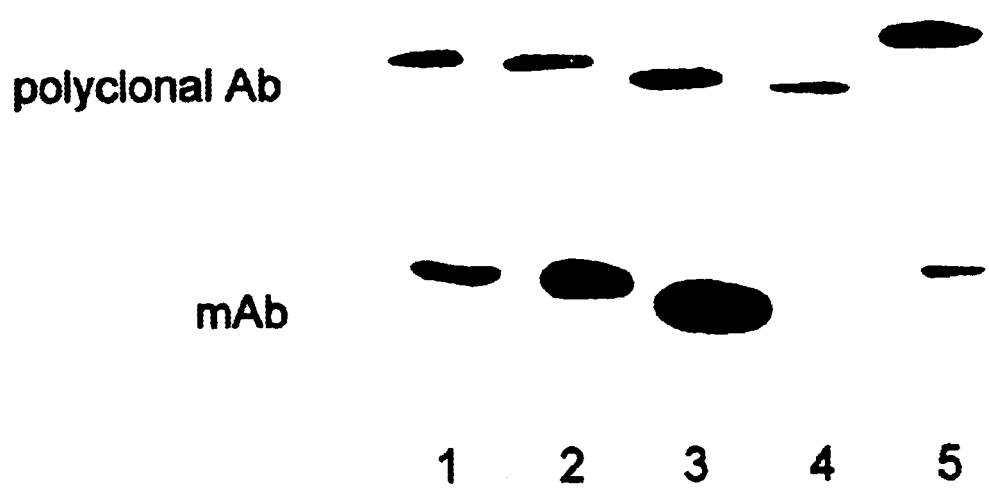
FIG. 6 depicts Western blot analysis of native and mutated rIL-16. Native rIL-16 and C-terminal IL-16 deletion mutant proteins were resolved by SDS/PAGE and transferred to nitrocellulose by electroblotting. Duplicate blots were probed with polyclonal rabbit anti-IL-16 (upper panel), or monoclonal anti-IL-16 (mAb 17.1; lower panel), detected with HRP-conjugated secondary Ab, and visualized by chemiluminescence. C-4 deletion (lane 1), C-8 (lane 2), C-12 (lane 3), C-16 (lane 4), native rIL-16 (lane 5).

Rabbit polyclonal anti-IL-16 Ab, as well as a murine monoclonal anti-IL-16 (clone 17.1) were generated using rIL-16 as an immunogen. This mAb was isolated by screening hybridoma supernatants for neutralization of IL-16 chemoattractant activity. Western blot analysis was performed with native rIL-16 and the C-terminal deletion mutants (FIG. 6), using either the polyclonal Ab or the mAb for detection. As expected, the polyclonal Ab recognized native rIL-16 and all of the deletion mutants. The mAb 17.1 detected native rIL-16 and the deletion mutants lacking 4, 8, or 12 C-terminal residues, as well as the N-terminal deletion mutants. However, mAb 17.1 failed to bind to C-16. The epitope for the neutralizing anti-IL-16 mAb 17.1 therefore maps to the identical domain shown to be required for IL-16 chemoattractant activity by peptide inhibition and mutation experiments.

EXAMPLE 6

Inhibition of the Mixed Lymphocyte Reaction

Figure 7:
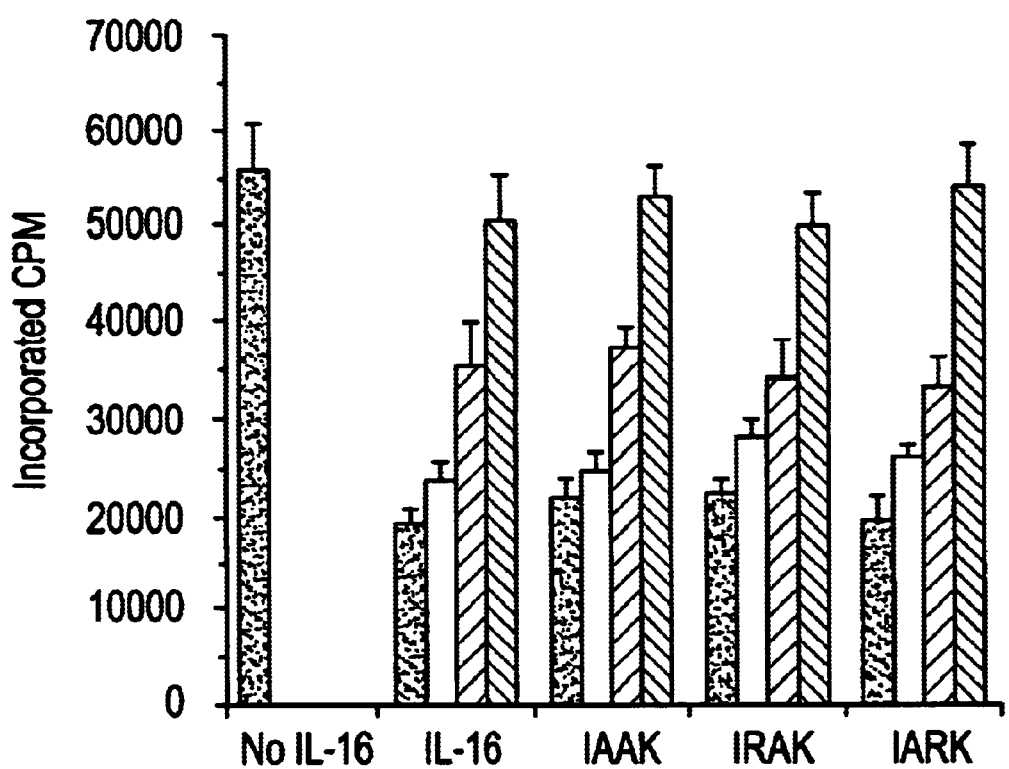
FIG. 7 depicts inhibition of the MLR by native rIL-16 or rIL-16 with C-terminal point mutations. Stimulator cells consisted of PBMC pre-treated with mitomycin C. Responder cells were T lymphocytes isolated from a different donor and incubated in control buffer (No IL-16), or pre-treated with native or mutated rIL-16 at $10^{-8}$ M (black bars), $10^{-9}$ M (empty bars), $10^{-10}$ M (crosshatched bars), or $10^{-11}$ M (stippled bars). The IL-16 point mutations included Arg$^{106}$ plus Arg$^{107}$ to alanine (IAAK), Arg$^{107}$ to alanine (IRAK), or Arg$^{106}$ to alanine (IARK). Cultures were pulsed with [$^3$H] thymidine on day 5 and harvested on day 6 for scintigraphy. Results are expressed as mean cpm (with background subtracted) ± SD for three experiments.
Figure 8:
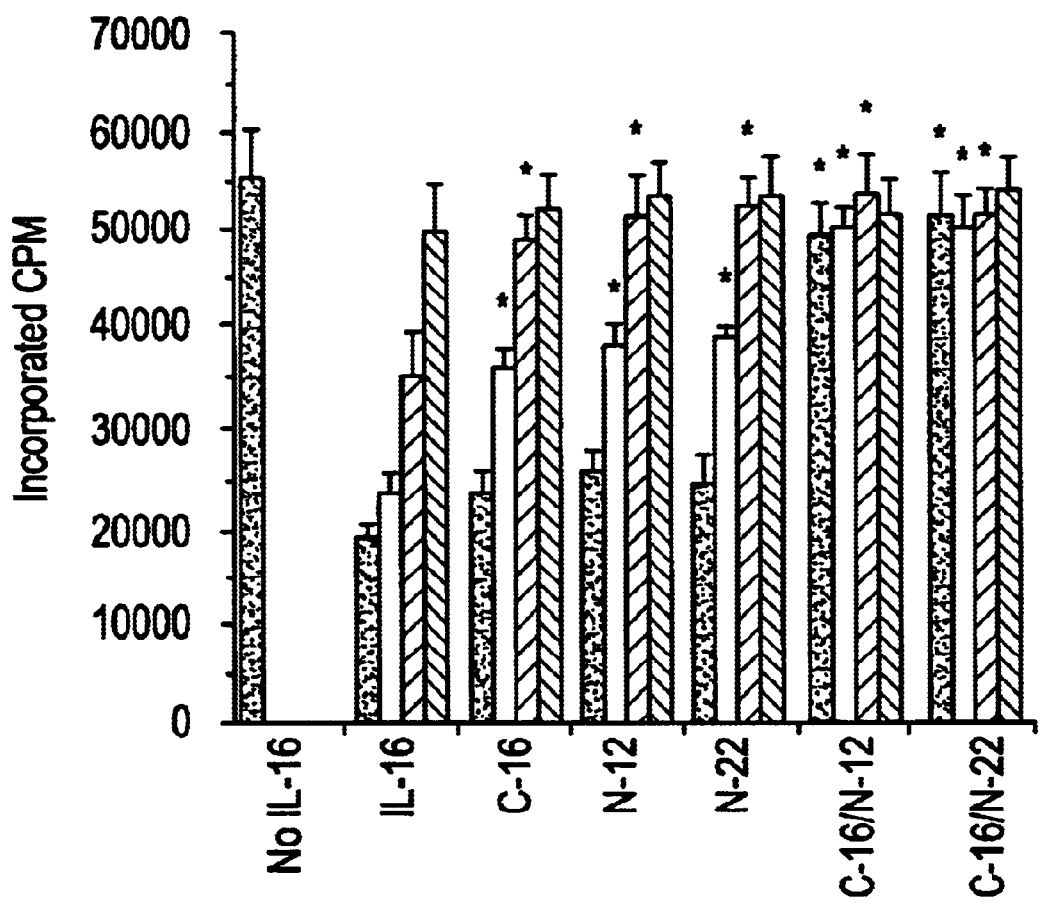
FIG. 8 depicts inhibition of MLR by IL-16 deletion mutants. Responder cells were pre-incubated in control buffer (No IL-16) or pre-treated with ($10^{-8}$ M to $10^{-11}$ M) native rIL-16 or with the rIL-16 deletion constructs C-12, C-16, N-12, N-22, C-16 plus N-12, or C-16 plus N-22. Asterisks indicate a significant difference (P<0.05) in mean cpm comparing cells pre-treated with native rIL-16 or mutated rIL-16 at the identical concentration.

To determine whether other biological activities of IL-16 are mediated by the C-terminal domain, the native and mutated rIL-16 constructs were tested for their capacity of inhibiting the one way MLR. Responder T lymphocytes were pre-treated with rIL-16 or control buffer, then cultured with mitomycin C-treated stimulator PBMC from an unrelated donor. Pre-treatment with $10^{-8}$ M native rIL-16 reduced thymidine incorporation on day 6 by nearly 70%, compared with untreated cells. Surprisingly, IL-16 mutants with the C-terminal point mutations which lost chemoattractant activity retained full capacity to inhibit the MLR (FIG. 7). The C-16 deletion mutant was nearly as active as native rIL-16, with a ~1 log shift of the dose response (FIG. 8). Deletion of 12 or 22 N-terminal residues resulted in a similar pattern as C-16; MLR inhibition was reduced but not eliminated. In contrast, constructs that combined the C-16 deletion with N-12 or N-22 lost all capacity to inhibit the MLR.

These data demonstrate that both N-terminal and C-terminal domains of IL-16 are involved in receptor binding and activation, and that the structural elements of IL-16 required for stimulating T cell motility are different from those required for inhibition of Mixed Lymphocyte Reaction.

TABLE I

| Seq ID | Sequence | Source |
|---|---|---|
| 1 | $X_{aa0}RX_{aa1}X_{aa2}$ | |
| 2 | RRKS | h, ag, rm, mac, man, z |
| 3 | RRTS | m |
| 4 | KRKS | sm, at |
| 5 | RRAS | analog |
| 6 | RRKA | analog |
| 7 | RRTA | analog |
| 8 | $X_{aa1}X_{aa2}X_{aa0}R$ | |
| 9 | VIRR | h, m, ag, rm, mac, man |
| 10 | VLRR | z |
| 11 | VIKR | sm, at |
| 12 | $X_{aa1}X_{aa0}RX_{aa2}$ | |
| 13 | IRRK | h, ag, rm, mac, man |
| 14 | IRRT | m |
| 15 | LRRK | z |
| 16 | IKRK | sm, at |
| 17 | RRKSLQ | h, ag, rm, mac, man |
| 18 | RRTSLQ | m |
| 19 | RRKSCM | z |
| 20 | KRKSMQ | sm, at |
| 21 | RRASLQ | analog |
| 22 | RRKALQ | analog |
| 23 | RRTALQ | analog |
| 24 | RRKSLQSK | h |
| 25 | RRTSLQCK | m |
| 26 | RRKSLQPK | ag, rm, man |
| 27 | RRKSCMSK | z |
| 28 | KRKSMQSK | sm, at |
| 29 | RRASLQSK | analog |
| 30 | RRKALQSK | analog |
| 31 | RRTALQCK | analog |
| 32 | RRASLQCK | analog |
| 33 | RRKSLQSKETTAAGDS | h |
| 34 | RRTSLQCKQTTASADS | m |
| 35 | RRASLQSKETTAAGDS | analog |
| 36 | RRKALQSKETTAAGDS | analog |
| 37 | RRTALQCKQTTASADS | analog |
| 38 | RRASLQCKQTTASADS | analog |
| 39 | Human IL-16 | |
| 40 | Murine IL-16 | |
| 41 | African green monkey IL-16 = rhesus monkey = mangeby | |
| 42 | macaque IL-16 | |
| 43 | zebu IL-16 | |
| 44 | squirrel monkey IL-16 | |
| 45 | *Aotus trivirgatus* IL-16 | |
| 46 | ETTAAGDS | |
| 47 | RSQRLK | |
| 48 | LQSK | |

Abbreviations:

h = human, m = murine, ag = African green monkey, rh = rhesus monkey, man = mangeby, z = zebu, mac = macaque, sm = squirrel monkey, at = *Aotus trivirgatus*

We claim:

1. An isolated Interleukin-16 (IL-16) antagonist peptide selected from the group consisting of RRKS (SEQ ID NO:2), RRTS (SEQ ID NO:3), KRKS (SEQ ID NO:4), RRAS (SEQ ID NO:5), RRKA (SEQ ID NO:6) and RRTA (SEQ ID NO:7).

2. An isolated IL-16 antagonist peptide selected from the group consisting of RRKSLQ (SEQ ID NO:17), RRTSLQ (SEQ ID NO:18), RRKSCM (SEQ ID NO:19), KRKSMQ (SEQ ID NO:20), RRASLQ (SEQ ID NO:21), RRKALQ (SEQ ID NO:22) and RRTALQ (SEQ ID NO:23).

3. An isolated IL-16 antagonist peptide selected from the group consisting of RRKSLQSK (SEQ ID NO:24), RRTSLQCK (SEQ ID NO:25), RRKSLQPK (SEQ ID NO:26), RRKSCMSK (SEQ ID NO:27), KRKSMQSK (SEQ ID NO:28), RRASLQSK (SEQ ID NO:29), RRKALQSK (SEQ ID NO:30), RRTALQCK (SEQ ID NO:31) and RRASLQCK (SEQ ID NO:32).

4. An isolated IL-16 antagonist peptide selected from the group consisting of RRTSLQCKQTTASADS (SEQ ID NO:34), RRASLQSKETTAAGDS (SEQ ID NO:35), RRKALQSKETTAAGDS (SEQ ID NO:36), RRTALQCK-QTTASADS (SEQ ID NO:37) and RRASLQCKQT-TASADS (SEQ ID NO:38).

5. An isolated IL-16 antagonist peptide comprising $X_{aa0}RX_{aa1}X_{aa2}$ (SEQ ID NO:1), wherein $X_{aa0}$ is Lys, and $X_{aa1}$ and $X_{aa2}$ are any amino acids.

6. The isolated IL-16 antagonist peptide of claim 5, wherein $X_{aa1}$ is selected from Lys, Thr, or Ala; and $X_{aa2}$ is selected from Serine or Ala.

7. An isolated IL-16 antagonist peptide comprising $X_{aa0}RX_{aa1}X_{aa2}$ (SEQ ID NO:1), wherein $X_{aa0}$ is Arg and wherein said peptide consists of fewer than 16 amino acids.

8. The isolated IL-16 antagonist peptide of claim 7, wherein $X_{aa1}$ is selected from Lys, Thr, or Ala; and $X_{aa2}$ is Ser or Ala.

9. An isolated IL-16 antagonist peptide comprising a sequence selected from the group consisting of RRTS (SEQ ID NO:3), KRKS (SEQ ID NO:4), RRAS (SEQ ID NO:5), RRKA (SEQ ID NO:6) and RRTA (SEQ ID NO:7).

10. An isolated IL-16 antagonist peptide comprising $X_{aa1}X_{aa2}X_{aa0}R$ (SEQ ID NO:8), wherein $X_{aa0}$ is Arg or Lys, and $X_{aa1}$ and $X_{aa2}$ are any amino acids.

11. The isolated IL-16 antagonist peptide of claim 10, wherein $X_{aa1}$ is Val and $X_{aa2}$ is Ile or Leu.

12. The isolated IL-16 antagonist peptide of claim 10, wherein $X_{aa0}$ is Arg.

13. The isolated IL-16 antagonist peptide of claim 12, wherein $X_{aa1}$ is Val and $X_{aa2}$ is Ile or Leu.

14. The isolated IL-16 antagonist peptide of claim 10, wherein $X_{aa0}$ is Lys.

15. The isolated IL-16 antagonist peptide of claim 14, wherein $X_{aa1}$ is Val and $X_{aa2}$ is Leu or Ile.

16. The isolated IL-16 antagonist peptide of claim 12 or 14, wherein the tetrameric sequence coincides with the native sequence of a mammalian IL-16.

17. An isolated IL-16 antagonist peptide comprising a sequence selected from the group consisting of VIRR (SEQ ID NO:9), VLRR (SEQ ID NO:10) and VIKR (SEQ ID NO:11).

18. An isolated IL-16 antagonist peptide comprising $X_{aa1}X_{aa0}RX_{aa2}$ (SEQ ID NO:12), wherein $X_{aa0}$ is Arg or Lys, and $X_{aa1}$ and $X_{aa2}$ are any amino acids.

19. The isolated IL-16 antagonist peptide of claim 18, wherein $X_{aa1}$ is Ile or Leu and $X_{aa2}$ is Lys, Thr or Ala.

20. The isolated IL-16 antagonist peptide of claim 18, wherein $X_{aa0}$ is Arg.

21. The isolated IL-16 antagonist peptide of claim 20, wherein $X_{aa1}$ is selected from Ile or Leu and $X_{aa2}$ is Lys, Thr or Ala.

22. The isolated IL-16 antagonist peptide of claim 18, wherein $X_{aa0}$ is Lys.

23. The isolated IL-16 antagonist peptide of claim 22, wherein $X_{aa1}$ is selected from Leu or Ile; and $X_{aa2}$ is Lys, Thr or Ala.

24. The isolated IL-16 antagonist peptide of claim 20 or 22, wherein the tetrameric sequence coincides with the native sequence of a mammalian IL-16.

25. An isolated IL-16 antagonist peptide comprising a sequence selected from the group consisting of IRRK (SEQ ID NO:13), IRRT (SEQ ID NO:14), LRRK (SEQ ID NO:15) and IKRK (SEQ ID NO:16).

26. An isolated IL-6 antagonist peptide comprising a sequence selected from the group consisting of RRTSLQ (SEQ ID NO:18), RRKSCM (SEQ ID NO:19), KRKSMQ (SEQ ID NO:20), RRASLQ (SEQ ID NO:21), RRKALQ (SEQ ID NO:22) and RRTALQ (SEQ ID NO:23).

27. An isolated IL-16 antagonist peptide comprising a sequence selected from the group consisting of RRTSLQCK (SEQ ID NO:25), RRKSLQPK (SEQ ID NO:26), RRKSC-MSK (SEQ ID NO:27), KRKSMQSK (SEQ ID NO:28), RRASLQSK (SEQ ID NO:29), RRKALQSK (SEQ ID NO:30), RRTALQCK (SEQ ID NO:31) and RRASLQCK (SEQ ID NO:32).

28. An isolated IL-16 antagonist peptide comprising a sequence selected from the group consisting of RRTSLQCKQTTASADS (SEQ ID NO:34), RRASLQS-KETTAAGDS. (SEQ ID NO:35), RRKALQSKET-TAAGDS (SEQ ID NO:36), RRTALQCKQTFASADS (SEQ ID NO:37) and RRASLQCKQTTASADS (SEQ ID NO:38).

29. A pharmaceutical composition comprising the isolated peptide of SEQ ID NO:24 and a pharmaceutically acceptable carrier.

30. An isolated IL-16 antagonist peptide comprising a sequence selected from the group consisting of RRKS (SEQ ID NO:2), RRKSLQ (SEQ ID NO:17), and RRKSLQSK (SEQ ID NO:24), wherein said peptide consists of fewer than 16 amino acids.

31. An isolated nucleic acid molecule coding for the isolated peptide according to any one of claims 1–3, 5, 7, 10, 18, or 20.

32. A composition comprising the isolated peptide of any of claims 1–3, 5, 7, 10, 18, or 30 and a pharmaceutically acceptable carrier.

* * * * *

SEQUENCE LISTING

<160> NUMBER OF SEQ ID NOS: 48

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Peptide
<220> FEATURE:
<221> NAME/KEY: UNSURE
<222> LOCATION: (1)
<223> OTHER INFORMATION: Xaa is Arg or Lys
<220> FEATURE:
<221> NAME/KEY: UNSURE
<222> LOCATION: (3)..(4)
<223> OTHER INFORMATION: Xaa can be any amino acid

<400> SEQUENCE: 1

Xaa Arg Xaa Xaa
 1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 2

Arg Arg Lys Ser
 1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 3

Arg Arg Thr Ser
 1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 4

Lys Arg Lys Ser
 1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 5

Arg Arg Ala Ser
 1

<210> SEQ ID NO 6

```
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 6

Arg Arg Lys Ala
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 7

Arg Arg Thr Ala
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:Peptide
<220> FEATURE:
<221> NAME/KEY: UNSURE
<222> LOCATION: (1)..(2)
<223> OTHER INFORMATION: Xaa can be any amino acid
<220> FEATURE:
<221> NAME/KEY: UNSURE
<222> LOCATION: (3)
<223> OTHER INFORMATION: Xaa is Arg or Lys

<400> SEQUENCE: 8

Xaa Xaa Xaa Arg
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 9

Val Ile Arg Arg
  1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 10

Val Leu Arg Arg
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:Peptide
```

```
<400> SEQUENCE: 11

Val Ile Lys Arg
 1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:Peptide
<220> FEATURE:
<221> NAME/KEY: UNSURE
<222> LOCATION: (1)
<223> OTHER INFORMATION: Xaa can be any amino acid
<220> FEATURE:
<221> NAME/KEY: UNSURE
<222> LOCATION: (2)
<223> OTHER INFORMATION: Xaa is Arg or Lys
<220> FEATURE:
<221> NAME/KEY: UNSURE
<222> LOCATION: (4)
<223> OTHER INFORMATION: Xaa can be any amino acid

<400> SEQUENCE: 12

Xaa Xaa Arg Xaa
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 13

Ile Arg Arg Lys
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 14

Ile Arg Arg Thr
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 15

Leu Arg Arg Lys
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 16
```

```
Ile Lys Arg Lys
  1

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 17

Arg Arg Lys Ser Leu Gln
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 18

Arg Arg Thr Ser Leu Gln
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 19

Arg Arg Lys Ser Cys Met
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 20

Lys Arg Lys Ser Met Gln
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 21

Arg Arg Ala Ser Leu Gln
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 22

Arg Arg Lys Ala Leu Gln
```

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 23

Arg Arg Thr Ala Leu Gln
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 24

Arg Arg Lys Ser Leu Gln Ser Lys
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 25

Arg Arg Thr Ser Leu Gln Cys Lys
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 26

Arg Arg Lys Ser Leu Gln Pro Lys
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 27

Arg Arg Lys Ser Cys Met Ser Lys
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 28

Lys Arg Lys Ser Met Gln Ser Lys
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 29

Arg Arg Ala Ser Leu Gln Ser Lys
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 30

Arg Arg Lys Ala Leu Gln Ser Lys
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 31

Arg Arg Thr Ala Leu Gln Cys Lys
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 32

Arg Arg Ala Ser Leu Gln Cys Lys
 1               5

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence:Peptide

<400> SEQUENCE: 33

Arg Arg Lys Ser Leu Gln Ser Lys Glu Thr Thr Ala Ala Gly Asp Ser
 1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence:Peptide

<400> SEQUENCE: 34

Arg Arg Thr Ser Leu Gln Cys Lys Gln Thr Thr Ala Ser Ala Asp Ser
 1               5                  10                  15

```
<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence:Peptide

<400> SEQUENCE: 35

Arg Arg Ala Ser Leu Gln Ser Lys Glu Thr Thr Ala Ala Gly Asp Ser
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence:Peptide

<400> SEQUENCE: 36

Arg Arg Lys Ala Leu Gln Ser Lys Glu Thr Thr Ala Ala Gly Asp Ser
 1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence:Peptide

<400> SEQUENCE: 37

Arg Arg Thr Ala Leu Gln Cys Lys Gln Thr Thr Ala Ser Ala Asp Ser
 1               5                  10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence:Peptide

<400> SEQUENCE: 38

Arg Arg Ala Ser Leu Gln Cys Lys Gln Thr Thr Ala Ser Ala Asp Ser
 1               5                  10                  15

<210> SEQ ID NO 39
<211> LENGTH: 121
<212> TYPE: PRT
<213> ORGANISM: Homo sapiens

<400> SEQUENCE: 39

Ser Ala Ala Ser Ala Ser Ala Ala Ser Asp Val Ser Val Glu Ser Thr
 1               5                  10                  15

Ala Glu Ala Thr Val Cys Thr Val Thr Leu Glu Lys Met Ser Ala Gly
                20                  25                  30

Leu Gly Phe Ser Leu Glu Gly Gly Lys Gly Ser Leu His Gly Asp Lys
            35                  40                  45

Pro Leu Thr Ile Asn Arg Ile Phe Lys Gly Ala Ala Ser Glu Gln Ser
        50                  55                  60

Glu Thr Val Gln Pro Gly Asp Glu Ile Leu Gln Leu Gly Gly Thr Ala
 65                 70                  75                  80

Met Gln Gly Leu Thr Arg Phe Glu Ala Trp Asn Ile Ile Lys Ala Leu
                85                  90                  95

Pro Asp Gly Pro Val Thr Ile Val Ile Arg Arg Lys Ser Leu Gln Ser
```

-continued

```
                100                 105                 110
Lys Glu Thr Thr Ala Ala Gly Asp Ser
            115                 120

<210> SEQ ID NO 40
<211> LENGTH: 118
<212> TYPE: PRT
<213> ORGANISM: Mus musculus

<400> SEQUENCE: 40

Ser Ala Ala Ser Ala Ser Ala Ala Ser Asp Ile Ser Val Glu Ser Lys
  1               5                  10                  15

Glu Ala Thr Val Cys Thr Val Thr Leu Glu Lys Thr Ser Ala Gly Leu
             20                  25                  30

Gly Phe Ser Leu Glu Gly Gly Lys Gly Ser Leu His Gly Asp Lys Pro
         35                  40                  45

Leu Thr Ile Asn Arg Ile Phe Lys Gly Asp Arg Thr Gly Glu Met Val
     50                  55                  60

Gln Pro Gly Asp Glu Ile Leu Gln Leu Ala Gly Thr Ala Val Gln Gly
 65                  70                  75                  80

Leu Thr Arg Phe Glu Ala Trp Asn Val Ile Lys Ala Leu Pro Asp Gly
                 85                  90                  95

Pro Val Thr Ile Val Arg Arg Thr Ser Leu Gln Cys Lys Gln Thr
                100                 105                 110

Thr Ala Ser Ala Asp Ser
            115

<210> SEQ ID NO 41
<211> LENGTH: 121
<212> TYPE: PRT
<213> ORGANISM: Chlorocebus aethiops

<400> SEQUENCE: 41

Ser Ala Ala Ser Ala Ser Ala Ala Ser Asp Val Ser Val Glu Ser Ser
  1               5                  10                  15

Ala Glu Ala Thr Val Tyr Thr Val Thr Leu Glu Lys Met Ser Ala Gly
             20                  25                  30

Leu Gly Phe Ser Leu Glu Gly Gly Lys Gly Ser Leu His Gly Asp Lys
         35                  40                  45

Pro Leu Thr Ile Asn Arg Ile Phe Lys Gly Ala Ala Ser Glu Gln Ser
     50                  55                  60

Glu Thr Ile Gln Pro Gly Asp Glu Ile Leu Gln Leu Ala Gly Thr Ala
 65                  70                  75                  80

Met Gln Gly Leu Thr Arg Phe Glu Ala Trp Asn Ile Ile Lys Ala Leu
                 85                  90                  95

Pro Asp Gly Pro Val Thr Ile Val Arg Arg Lys Ser Leu Gln Pro
                100                 105                 110

Lys Glu Thr Thr Ala Ala Asp Ser
            115                 120

<210> SEQ ID NO 42
<211> LENGTH: 121
<212> TYPE: PRT
<213> ORGANISM: Macaca fascicularis

<400> SEQUENCE: 42

Ser Ala Ala Ser Ala Ser Ala Ala Ser Asp Val Ser Val Glu Ser Ser
  1               5                  10                  15
```

-continued

Ala Glu Ala Thr Val Tyr Thr Val Thr Leu Glu Lys Met Ser Ala Gly
            20                  25                  30

Leu Gly Phe Ser Leu Glu Gly Gly Lys Gly Ser Leu His Gly Asp Lys
        35                  40                  45

Pro Leu Thr Ile Asn Arg Ile Phe Lys Gly Ala Ala Ser Glu Gln Ser
    50                  55                  60

Glu Thr Ile Gln Pro Gly Asp Glu Ile Leu Gln Leu Ala Gly Thr Ala
65                  70                  75                  80

Met Gln Gly Leu Thr Arg Phe Glu Ala Trp Asn Ile Ile Lys Ala Leu
                85                  90                  95

Pro Asp Gly Pro Val Thr Thr Val Ile Arg Arg Lys Ser Leu Gln Pro
            100                 105                 110

Lys Glu Thr Thr Ala Ala Ala Asp Ser
        115                 120

<210> SEQ ID NO 43
<211> LENGTH: 118
<212> TYPE: PRT
<213> ORGANISM: Bos primigenius indicus

<400> SEQUENCE: 43

Ser Ser Gly Ser Ala Ser Val Asp Ser Glu Ser His Arg Ile Arg Glu
1               5                   10                  15

Ala Thr Val Cys Thr Val Thr Leu Glu Lys Thr Ser Ala Gly Leu Gly
            20                  25                  30

Phe Ser Leu Glu Gly Gly Lys Gly Ser Leu His Gly Asp Lys Leu Leu
        35                  40                  45

Thr Val Asn Arg Ile Leu Lys Gly Trp Leu Glu Gln Ser Asp Thr Val
    50                  55                  60

Gln Pro Gly Asp Glu Ile Val His Leu Ala Gly Thr Ala Met Gln Asp
65                  70                  75                  80

Leu Thr Arg Phe Glu Glu Trp Asn Ile Ile Lys Ala Leu Pro Asp Gly
                85                  90                  95

Pro Val Thr Ile Val Leu Arg Arg Lys Ser Cys Met Ser Lys Gly Thr
            100                 105                 110

Pro Ala Ala Gly Asp Pro
        115

<210> SEQ ID NO 44
<211> LENGTH: 120
<212> TYPE: PRT
<213> ORGANISM: Saimiri sciureus

<400> SEQUENCE: 44

Ser Ala Ala Ser Ala Ser Ala Ala Ser Asp Val Ser Val Asp Ser Thr
1               5                   10                  15

Ala Glu Ala Thr Val Cys Thr Val Thr Leu Glu Lys Met Ser Gly Gly
            20                  25                  30

Leu Gly Phe Ser Leu Glu Gly Gly Lys Gly Ser Leu Gln Gly Asp Lys
        35                  40                  45

Pro Leu Thr Ile Asn Arg Ile Phe Lys Gly Ala Ala Ser Glu Gln Ser
    50                  55                  60

Glu Thr Val Gln Pro Gly Asp Glu Ile Leu His Leu Ala Gly Thr Ala
65                  70                  75                  80

Met Gln Gly Leu Thr Arg Phe Glu Ala Trp Asn Ile Ile Lys Ala Leu
                85                  90                  95

```
Pro Asp Gly Pro Val Thr Ile Val Ile Lys Arg Lys Ser Met Gln Ser
            100                 105                 110

Lys Gly Thr Ser Ala Ala Gly Asp
        115                 120
```

<210> SEQ ID NO 45
<211> LENGTH: 121
<212> TYPE: PRT
<213> ORGANISM: Aotus trivirgatus

<400> SEQUENCE: 45

```
Ser Ala Ala Ser Val Ser Ala Ala Ser Asp Val Ser Val Asp Ser Thr
  1               5                  10                  15

Ala Glu Ala Thr Val Cys Thr Val Thr Leu Glu Lys Met Ser Gly Gly
                 20                  25                  30

Leu Gly Phe Ser Leu Glu Gly Gly Lys Gly Ser Leu His Gly Asp Lys
             35                  40                  45

Pro Leu Thr Ile Asn Arg Ile Phe Lys Gly Ala Ala Ser Glu Gln Ser
         50                  55                  60

Glu Thr Val Gln Pro Gly Asp Glu Ile Leu His Leu Ala Gly Thr Ala
 65                  70                  75                  80

Met Gln Gly Leu Thr Arg Phe Glu Ala Trp Asn Ile Ile Lys Ala Leu
                 85                  90                  95

Pro Asp Gly Pro Val Thr Ile Val Ile Lys Arg Lys Ser Met Gln Ser
            100                 105                 110

Lys Gly Thr Pro Ala Ala Gly Asp Ser
        115                 120
```

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence:Peptide

<400> SEQUENCE: 46

```
Glu Thr Thr Ala Ala Gly Asp Ser
  1               5
```

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:Peptide

<400> SEQUENCE: 47

```
Arg Ser Gln Arg Leu Lys
  1               5
```

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence:Peptide

<400> SEQUENCE: 48

```
Leu Gln Ser Lys
  1
```